(12) United States Patent
Årthun et al.

(10) Patent No.: US 8,029,023 B2
(45) Date of Patent: Oct. 4, 2011

(54) DEVICE AND METHOD FOR CONTAMINATION-FREE AND/OR STERILE SEALING BETWEEN AT LEAST TWO INTERCONNECTABLE CONNECTING MEANS

(75) Inventors: Nils Årthun, Sandnes (NO); Sten Johansson, Hisings Kärra (SE); Lennart Myhrberg, Älvängen (SE); Håkan Samuelsson, Onsala (SE)

(73) Assignee: Millipore AB, Solna (SE)

( * ) Notice: Subject to any disclaimer, the term of this patent is extended or adjusted under 35 U.S.C. 154(b) by 793 days.

(21) Appl. No.: 11/885,623

(22) PCT Filed: Feb. 8, 2006

(86) PCT No.: PCT/SE2006/000169
§ 371 (c)(1),
(2), (4) Date: May 5, 2008

(87) PCT Pub. No.: WO2006/093450
PCT Pub. Date: Sep. 8, 2006

(65) Prior Publication Data
US 2008/0277878 A1 Nov. 13, 2008

(30) Foreign Application Priority Data
Mar. 4, 2005 (SE) ...................... 0500493

(51) Int. Cl.
*F16L 35/00* (2006.01)
(52) U.S. Cl. ............. 285/67; 285/68; 604/905; 604/533
(58) Field of Classification Search ................ 285/4, 67, 285/68, 71, 3, 99, 100, 109, 352; 604/905, 604/533
See application file for complete search history.

(56) References Cited

U.S. PATENT DOCUMENTS

| | | | |
|---|---|---|---|
| 3,909,910 A | 10/1975 | Rowe et al. | |
| 4,019,512 A * | 4/1977 | Tenczar | 604/905 |
| 4,187,846 A * | 2/1980 | Lolachi et al. | 604/905 |
| 4,253,684 A | 3/1981 | Tolbert et al. | |
| 4,418,945 A | 12/1983 | Kellogg | |

(Continued)

FOREIGN PATENT DOCUMENTS
WO    WO-98/50105    11/1998
(Continued)

OTHER PUBLICATIONS
EP Search Report for Application No. 06716870.8.

*Primary Examiner* — David E Bochna
(74) *Attorney, Agent, or Firm* — Dickstein Shapiro LLP

(57) ABSTRACT

A method and a device are provided for contamination-free and/or sterile sealing between two interconnectable connecting elements having opposing openings. Interconnection allows transfer of a fluid between the openings. Sealing elements are arranged on the connecting elements around the openings, and protective films are provided, covering the sealing elements and the openings and adapted to be removed in the final interconnection. The sealing elements are each provided with at least one recess which extends wholly or partly around the associated opening and receives a gas. In use the sealing elements are moved into engagement with each other, interleaved with the protective films, to reduce the volume of the recesses and, thus, increase the pressure of the gas therein. During removal of the protective films, the gas flows out of the recesses to the environment to prevent penetration of contamination into the openings.

27 Claims, 5 Drawing Sheets

U.S. PATENT DOCUMENTS

| | | | |
|---|---|---|---|
| RE32,056 E | 12/1985 | Granzow et al. | |
| 5,492,147 A * | 2/1996 | Challender et al. | 604/905 |
| 6,077,259 A * | 6/2000 | Caizza et al. | 604/905 |
| 6,536,805 B2 * | 3/2003 | Matkovich | 604/905 |
| 6,880,801 B2 * | 4/2005 | Matkovich et al. | 604/905 |
| 7,090,191 B2 * | 8/2006 | Matkovich et al. | 604/905 |
| 7,523,918 B2 * | 4/2009 | Matkovich et al. | 604/415 |
| 7,678,096 B2 * | 3/2010 | Biddel et al. | 604/403 |
| 2003/0030272 A1 | 2/2003 | Johnson et al. | |

FOREIGN PATENT DOCUMENTS

| | | |
|---|---|---|
| WO | WO-2005/016443 | 2/2005 |

* cited by examiner

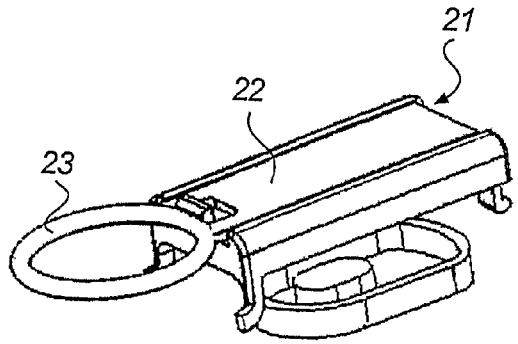
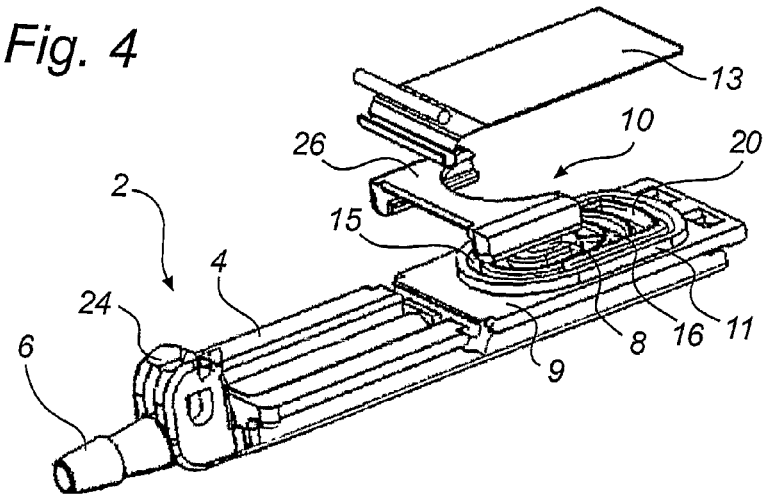
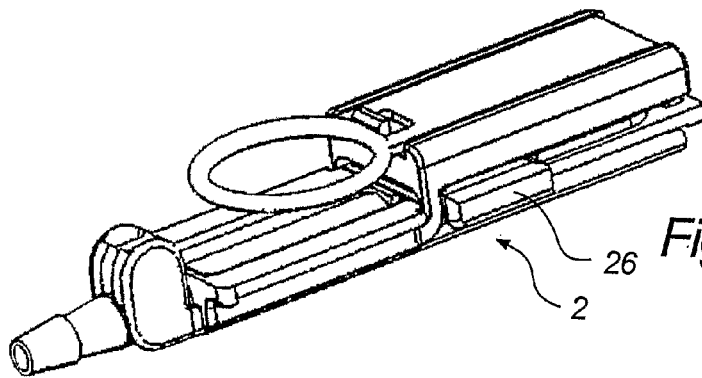
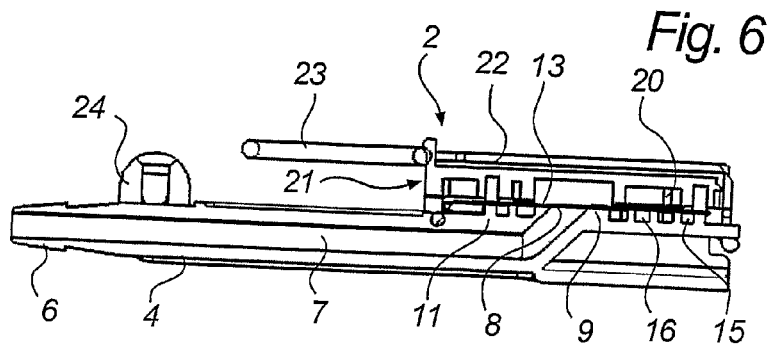

DEVICE AND METHOD FOR CONTAMINATION-FREE AND/OR STERILE SEALING BETWEEN AT LEAST TWO INTERCONNECTABLE CONNECTING MEANS

FIELD OF THE INVENTION

The present invention relates generally to a sealing method and a sealing device preferably of the disposable type to be used in a variety of fields, for instance in the pharmaceutical, food and biotechnology fields, and also in other contexts such as handling of pharmaceutical preparations on patients, blood handling, handling of cytostatics, where the safety of the operator is important, handling of fluids in the semiconductor and aerospace industry etc.

More specifically, the invention relates to a method for contamination-free and/or sterile sealing between at least two interconnectable connecting means with opposing openings to allow, after interconnection, transfer of a fluid between them, sealing elements being arranged on the connecting means around the openings and provided with protective films covering the sealing elements and the openings and adapted to be removed in the final interconnection.

The invention also relates to a device for contamination-free and/or sterile sealing between at least two interconnectable connecting means with opposing openings to allow, after interconnection, transfer of a fluid between them, the device having sealing elements which are arranged on the connecting means around the openings and are provided with protective films which cover the sealing elements and the openings and are removable in the final interconnection.

BACKGROUND ART

In many fields, of which a few have been mentioned above as examples, it is normally necessary to transfer fluids from one process unit, such as a vessel or bag of a conventional type or of a now more common disposable type, to another or to other equipment without these fluids risking to be contaminated with foreign particles, especially airborne bacteria and the like or gaseous air pollutants. In the fields above, there is, inter alia, a more or less continuous need for sampling of fluids, for instance for microbiological control, cell counting or various chemical analyses, or supply of regulating or active substances, for instance a pH buffer or a biological starter culture, in certain process steps in the manufacture of products in the respective fields. Whenever a new connection for the purposes above has to be made to transfer fluids from one vessel to another, there is a great risk of contamination of the fluids, especially in non-sterile spaces.

Such connection can occur by introducing a sterile needle connected to one vessel via a tube or pipe, into a sterile membrane connected to the other vessel. In the interconnection, the connecting components and/or the fluids are exposed to the risk of being contaminated with airborne bacteria, spores etc. and by incorrect handling of the connecting components.

To reduce the risk of contamination when interconnecting two or more vessels for transfer of fluids between them, instead of the above-described needle connecting device, a sterile connector has been suggested, inter alia, by U.S. Pat. No. 3,909,910, with a device for sealing between two interconnectable connecting means included in the sterile connector, with opposing openings to allow, when interconnected, transfer of a fluid between them. The device has sealing elements, which are arranged on the connecting means around the openings and are provided with protective films covering the sealing elements and the openings and being removable in the final interconnection. With the connecting means arranged end-to-end with the openings opposite each other, and with the sealing elements pressed against each other during elastic deformation, the protective films engaging each other are manually pulled off at the same time from the connecting means.

When pulling off the protective films, they are folded back on themselves, and even if they are very thin there arises in the folding area a small gap with a width corresponding to the width of the protective films. This gap "moves" in the pull-off direction and passes the area of the openings in the sealing elements and the connecting means, so that airborne contamination is entrained by the gap and risks entering the openings and contaminating the fluid.

OBJECTS OF THE INVENTION

The main object of the present invention is to provide a method and a device of the type stated by way of introduction, which in a new and unique way effectively eliminate the above-described drawbacks and the risks of contamination of fluids when interconnecting two or more vessels or process units for fluid transfer between them.

Another object of the invention is to provide such a method and such a device, which result in a contamination-free and/or sterile sealing in such a manner that airborne bacteria, spores, microorganisms and other external contaminants cannot enter and mix with the fluids that are transferred between the connecting means.

A further object of the invention is to provide a method and a device where all conventional requirements are satisfied as to contamination-free transfer of the fluid all the way from one process unit/vessel to another and/or to supply of substances or sampling etc.

SUMMARY OF THE INVENTION

The above and other related objects of the invention are achieved in a simple as well as effective manner in the method according to the invention by at least one of the sealing elements being provided with at least one recess, which extends wholly or partly around the associated opening and receives a gas, the sealing elements being, when interconnecting the connecting means, moved into engagement with each other, interleaved with the protective films, to change the volume of the recess and, thus, change the pressure of the gas therein, and, in the subsequent quick removal of the protective films, the gas creating by its pressure a flow which prevents penetration of contamination into the openings in the final interconnection of the connecting means.

With respect to the device according to the invention, the above and other related objects are achieved in the same simple and effective manner by at least one of the sealing elements being provided with at least one recess, which extends wholly or partly around the associated opening and receives a gas, the sealing elements, when interconnecting the connecting means, being movable into engagement with each other, interleaved with the protective films, to change the volume of the recess and, thus, change the pressure of the gas therein, and, in the subsequent quick removal of the protective films, the gas creating by its pressure a flow which prevents penetration of contamination into the openings in the final interconnection of the connecting means.

In a preferred embodiment, the sealing elements are moved into engagement with each other to increase the volume of the recess or recesses and, thus, reduce the pressure of the gas therein, and, in the subsequent quick removal of the protective films, the gas sucks in additional gas to provide a flow which prevents penetration of contamination into the openings in the final interconnection of the connecting means.

In a still more preferred embodiment of the method, the sealing elements are moved into engagement with each other in order to instead reduce the volume of the recess or recesses and, thus, instead increase the pressure of the gas therein, and, in the subsequent quick removal of the protective films, the gas flows out of the recesses to prevent penetration of contamination into the openings in the final interconnection of the connecting means.

In a further development of the method, the sealing elements are preferably provided with at least two groups of recesses with different volumes, which cooperate in pairs and are positioned one outside the other and the sealing elements, when moved against each other, reduce the different volumes of the recesses and, thus, increase the pressure of the gas therein differently, so that the gas, in the removal of the protective films, flows from the group of recesses with the highest pressure to the group/groups of recesses with a lower pressure. Then the highest pressure is preferably generated in the innermost group of recesses and a successively decreasing pressure is generated in the group/groups of recesses outside these to force the gas in the direction of the environment.

It is then advantageous if the recesses in at least one group are divided into partial recesses to prevent all gas therein from flowing out before complete removal of the protective films.

Moreover, in a particularly preferred embodiment, there are arranged between the groups of recesses additional separate recesses with a limited extent to create, when starting to remove the protective films, an intensification of the gas flow in the direction of the environment.

It is particularly convenient to make preferably at least one of the sealing elements elastically yieldable so as to be expanded or compressed in the interconnection of the connecting means.

In the corresponding preferred embodiment of the device, the sealing elements are movable into engagement with each other to increase the volume of the recesses and, thus, reduce the pressure of the gas therein, and, in the subsequent quick removal of the protective films, the gas is caused to suck in additional gas and thus create a flow which prevents penetration of contamination into the openings in the final interconnection of the connecting means.

In the particularly preferred embodiment, the sealing means are movable into engagement with each other to reduce the volume of the recesses and, thus, increase the pressure of the gas therein, and, in the subsequent quick removal of the protective films, the gas is caused to flow out of the recesses and, thus, prevent penetration of contamination into the openings in the final interconnection of the connecting means.

The sealing elements are conveniently provided with at least two groups of recesses with different volumes, which cooperate in pairs and are positioned one outside the other. Then the sealing elements are caused, when being moved together, to reduce the different volumes of the recesses and, thus, increase the pressure of the gas therein differently. The gas is then, in the removal of the protective films, forced out of the group of recesses with the highest pressure to the group/groups of recesses with a lower pressure.

Then the highest pressure of the gas conveniently prevails in the innermost group of recesses and a successively decreasing pressure prevails in the group/groups of recesses outside these to force the gas in the direction of the environment.

Correspondingly, in the device according to the invention, the recesses in at least one group are suitably divided into partial recesses to prevent all gas therein from flowing out before complete removal of the protective films.

In a further development of the device according to the invention, additional separate recesses with a limited extent are suitably arranged between the groups of recesses to create, when starting to remove the protective films, an intensification of the gas flow in the direction of the environment.

In a preferred embodiment of the device, at least one of the sealing elements is preferably compressible in the interconnection of the connecting means, the compressible sealing element/sealing elements in one embodiment suitably having the form of inserts of an elastically yieldable material which are arranged in the associated connecting means.

In a particularly preferred further development of the device according to the invention, there is arranged, outside each sealing element, a substantially circumferential seal of an elastically yieldable material on the associated connecting means, on which seals the protective films are sealingly arranged at their outer edge and which seals, interleaved with the protective films, are movable into engagement with each other in the interconnection of the connecting means.

BRIEF DESCRIPTION OF THE DRAWINGS

The invention will now be described in more detail with reference to the accompanying drawings, in which FIG. 4 is an exploded side view, in oblique perspective corresponding to FIG. 1, of a second connector half included in the sterile connector, FIG. 5 illustrates in the same perspective view as FIG. 4 the second connector half in the assembled state, FIG. 6 is a central longitudinal section of the connector half according to FIG. 5, FIGS. 7-12 illustrate slightly schematically in an oblique side view in perspective successive steps for interconnecting the sterile connector according to FIGS. 1-6 to be ready for use.

DESCRIPTION OF A PREFERRED EMBODIMENT

Figure 1:
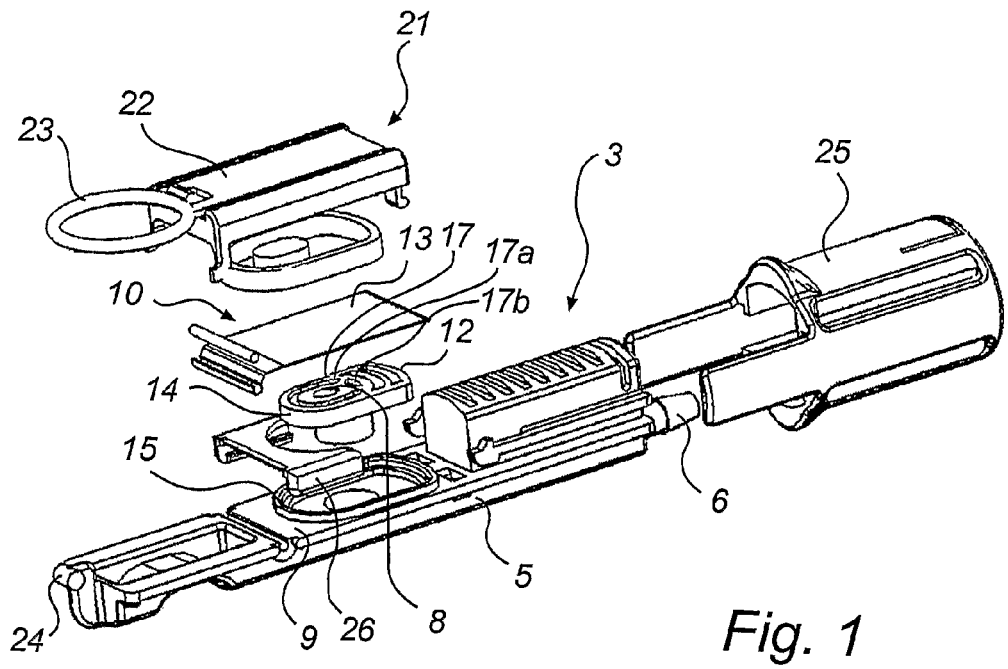
FIG. 1 is an exploded side view, in oblique perspective, of a first connector half included in a sterile connector.
Figure 2:
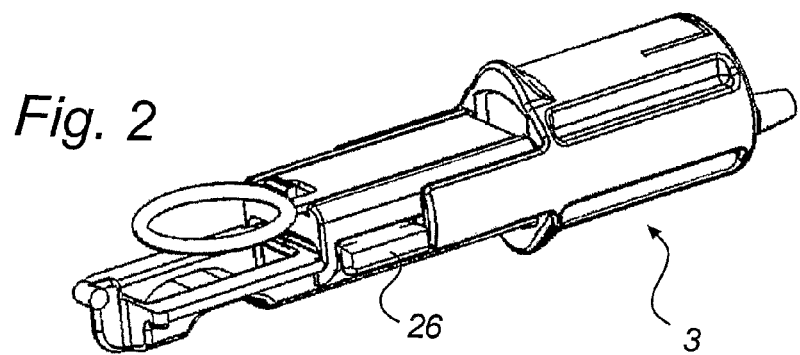
FIG. 2 illustrates in the same perspective view the connector half according to FIG. 1 in the assembled state.
Figure 3:
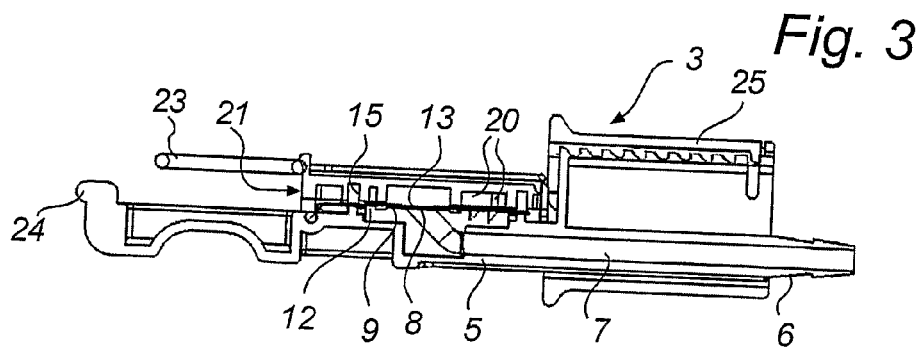
FIG. 3 is a central longitudinal section of the connector half according to FIG. 2.

The accompanying drawings illustrate a sterile connector generally designated 1, made of a suitable material such as plastic for presterilised connection, sealed against contamination, of two or more process units (not shown), such as receptacles/vessels of metal or rigid plastic or bags of non-rigid plastic of a conventional re-use type or of a disposable type, via tubes or pipes (not shown) preferably made of non-rigid plastic.

More specifically, the sterile connector 1 comprises as main components first and second connector halves 2, 3, also referred to as male and female parts. The connector halves 2, 3 each have an elongate connecting means 4 and 5, respectively, which at their outer free ends each have a nipple 6 to be connected to one end of the tubes (not shown). The other ends of the tubes are, in a manner not shown, connected to the associated process unit. As a variant, one of the connecting means 4, 5 can at its free end be directly connected to its process unit.

Each connecting means 4, 5 has an elongate through duct 7 which extends from the associated nipple 6 to an opening 8 towards the other ends of the connecting means 4, 5. The openings 8 open into substantially flat connecting planes 9 on one side of the connecting means and extend substantially in the longitudinal direction thereof. When interconnecting the two connecting means 4, 5 in a manner that will be described below, the openings 8 face each other and are positioned opposite each other in order to allow, after the interconnection, contamination-free transfer of a fluid (not shown), such as a gas or liquid or a mixture thereof, between them and thus the process units.

A device, generally designated 10, for contamination-free sealing between the two interconnectable connecting means 4, 5 has sealing elements 11, 12 which are each arranged on a connecting means around the associated opening 8 therein. The sealing elements 11, 12, which will be described in more detail below, are each provided with a protective film 13 of a very thin and yet very tight plastic. The protective films 13 cover the associated sealing element 11, 12 and opening 8 and are adapted to be removed in conjunction with the final interconnection of the connecting means 4, 5.

In the preferred embodiment shown in the drawings, at least the sealing element 12 arranged on the connecting means 5 of the second connector half 3, the female part, is compressible in the form of an insert 14 arranged in the connecting means and made of an elastically yieldable material such as plastic, rubber or the like, with elastic and sealing properties that are necessary for the purpose.

In the embodiment illustrated, a further, substantially circumferential seal 15 is arranged outside and around each sealing element 11, 12, which seal is also made of a suitable, elastically yieldable material such as plastic or rubber and is arranged on the associated connecting means 4, 5. The above-described protective films 13 are at their outer edge, that is along their periphery, in a sealing but tear-off manner, attached to the seals 15, for instance by gluing, welding or the like. In a manner that will be described below, the seals 15, interleaved with the protective films 13, are movable into engagement with each other in the interconnection of the connecting means 4, 5.

Referring once more to the sealing elements 11, 12 on the connecting means 4, 5, they are each provided with at least one recess 16 and 17, respectively, which has the form of a groove or depression and extends wholly or partly around the associated opening 8 in the connecting means 5, 6. The recesses 16, 17 receive or contain a gas 18, for instance an inert gas or a sterile gas, such as sterile air.

In the particularly preferred embodiment illustrated in the drawings, the sealing elements 11, 12 are provided with two groups of recesses 16, 17 with different volumes, positioned one outside the other and cooperating in pairs. However, there is nothing to prevent that there is only one recess 16, 17 or three or more recesses 16, 17 positioned one outside the other around the associated opening 8.

When interconnecting the connecting means 4, 5, the sealing elements 11, 12 are in the same way as the seals 15 movable into engagement with each other, interleaved with the protective films 13. When the connecting means 4, 5 are pressed against each other, the volume or the different volumes of the recesses 16, 17 is/are reduced, depending on the number of groups of recesses, thus increasing the pressure of the gas 18 therein evenly or differently for the same reasons.

When after that the protective films 13 are, in a manner described below, quickly removed or torn off simultaneously and jointly from the sealing elements 11, 12 and the seals 15, the pressure increase in the recesses 16, 17 forces the gas 18 out of the recesses, thus preventing penetration of contamination into the openings 8 of the connecting means 4, 5 in the final interconnection of these means.

In the preferred embodiment with two or more groups of recesses 16, 17 arranged one outside the other and where the highest gas pressure prevails in the innermost group and a successively decreasing gas pressure prevails in the group or groups outside the same, the gas 18 is forced, when removing the protective films, out of the group with the highest pressure to the group or groups with a lower pressure outwards to the environment 19.

To prevent not all the gas 18 in the recesses 16, 17 from flowing out before complete removal of the protective films 13, the recesses in at least one group, in the shown embodiment preferably both, can be divided into partial recesses 16a and 16b regarding the recesses 16, and 17a and 17b regarding the recesses 17.

To create, when starting to remove the protective films 13, an intensification of the gas flow in the direction of the environment 19, there are in the shown embodiment additional, separate recesses 20 with a limited extent in the longitudinal direction in the sealing elements 11, 12 between the above-described groups of recesses 16, 17.

The function and handling of the above-described sterile connector 1 will now be briefly described step by step with special reference to FIGS. 7-12.

Figure 7:
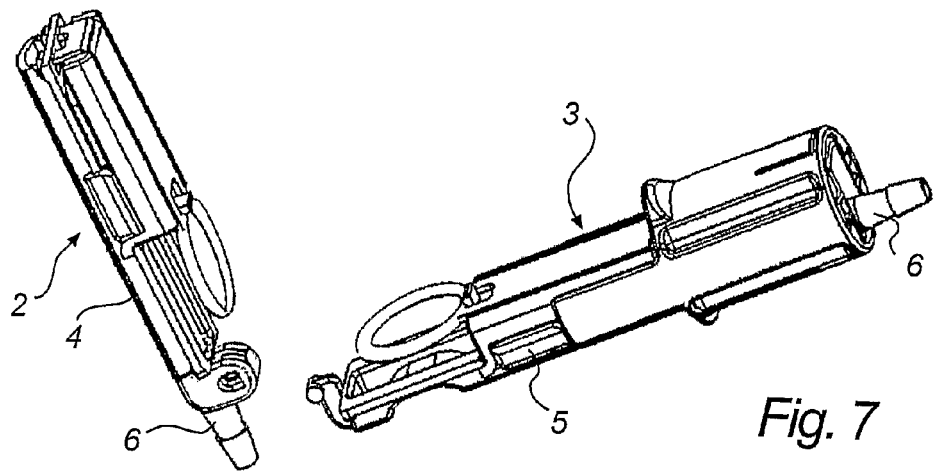

FIG. 7 shows step 1, the starting position, where the connector halves 2, 3 of the sterile connector 1 have been removed separately from their respective sterile transport and storage packages and where the connecting tubes (not shown) are connected to the respective nipples 6.

Figure 8:
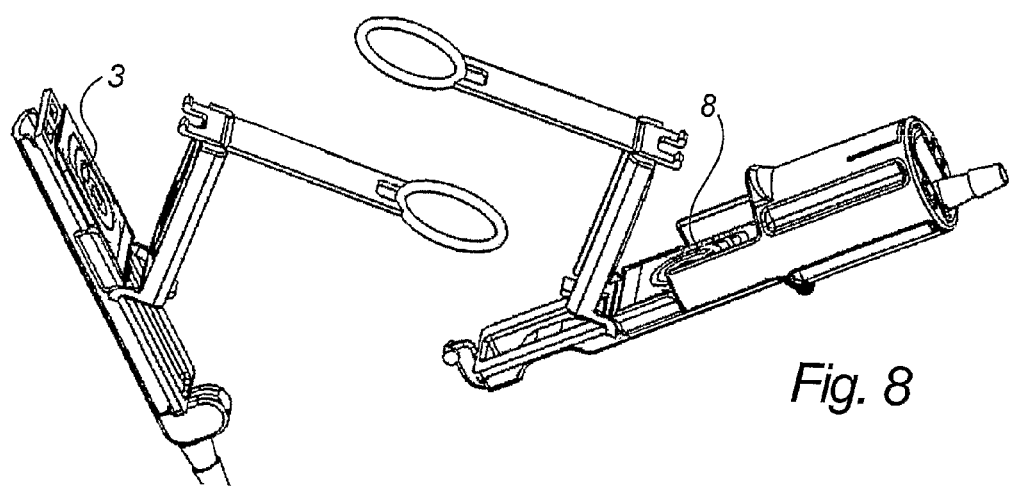
Figure 9:
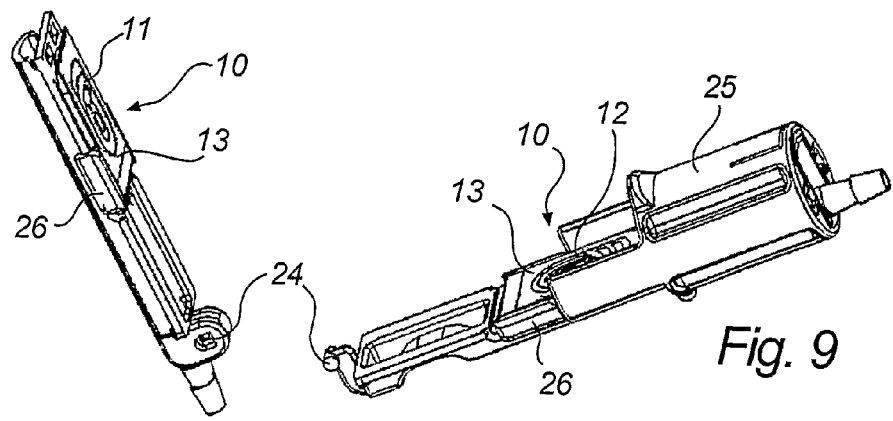

In step 2, see FIG. 8, protective covers 21 over the sealing elements 11, 12 on the connecting means 4, 5 of the connector halves 2, 3 are each removed by means of an opener 22 with a pull ring 23. Step 3 in FIG. 9 is now reached.

Figure 10:
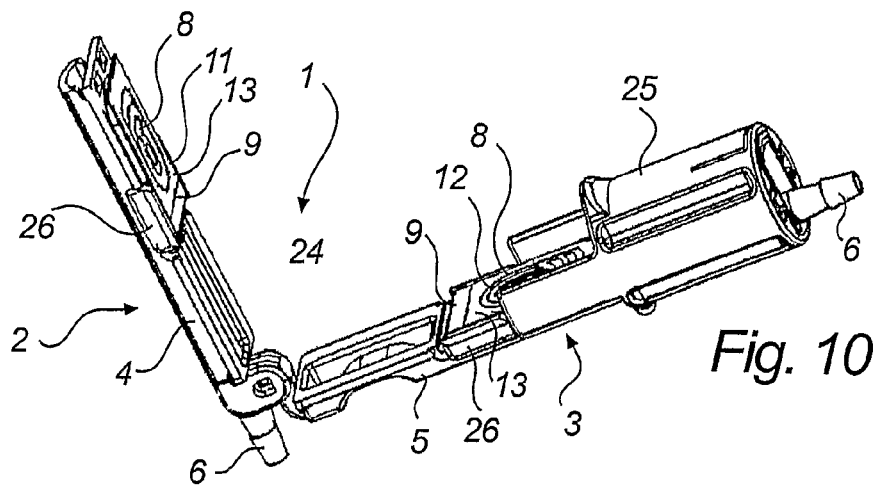

Step 4 is shown in FIG. 10, where the connector halves 2, 3 are articulated to each other by a hinge 24 by snap action.

Figure 11:
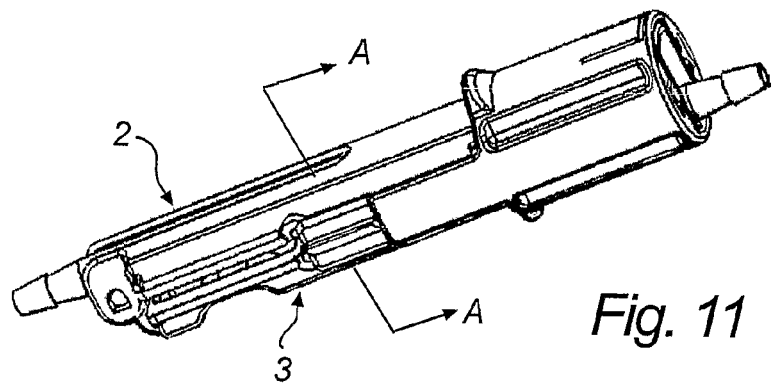

FIG. 11 illustrates step 5, where the connecting planes 9 of the connecting means 4, 5 of the connector halves 2, 3 are moved into engagement with each other by pivoting the connector halves towards each other via the hinge 24 until the first connector half 2 with its outer free end snaps under a locking sleeve 25 which is longitudinally guided on the second connector half 3.

Figure 12:
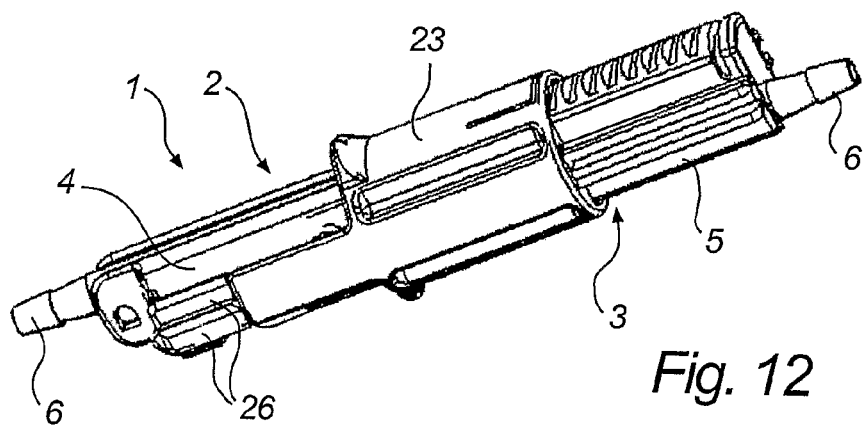
Figure 13:
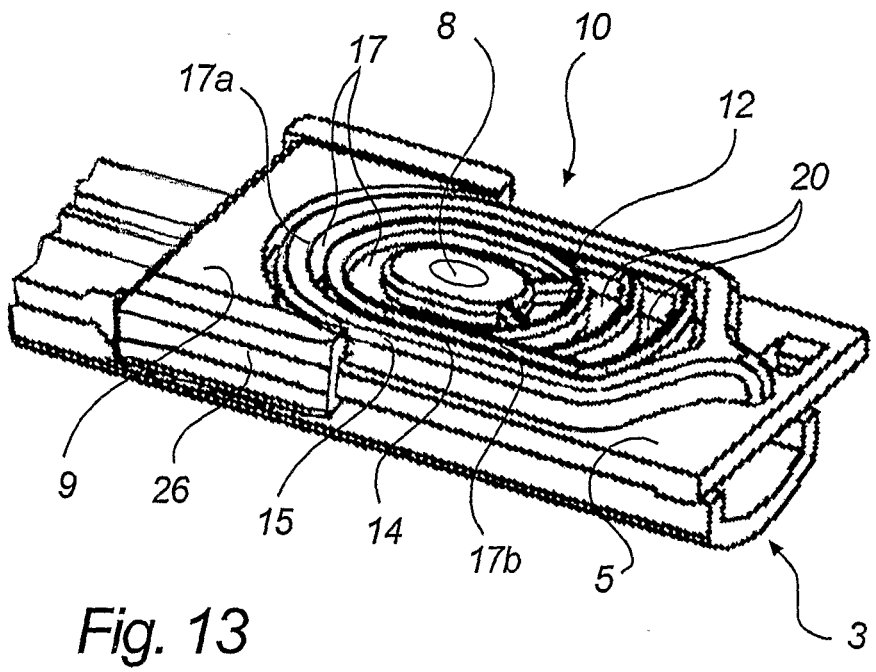
FIG. 13 is a perspective view, obliquely from above, of a portion of the first connector half and illustrates in more detail the design and location of a sealing element included in a sealing device according to the invention.
Figure 14:
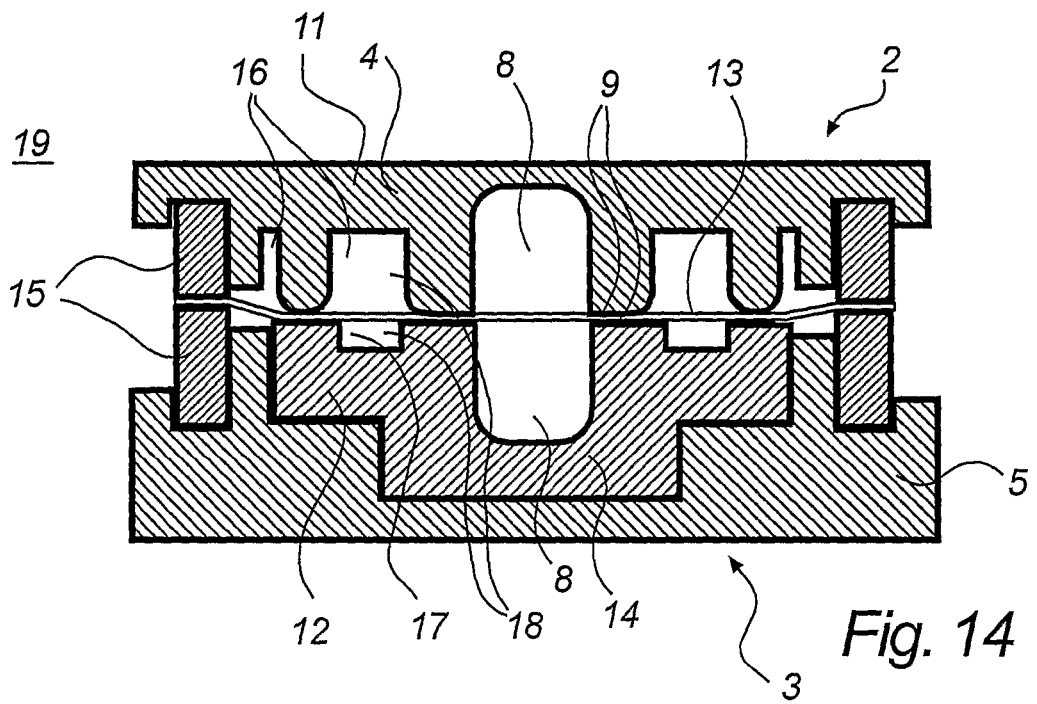
FIG. 14 shows schematically and in section substantially along line A-A in FIG. 11 the function of and cooperation between the sealing element according to FIG. 13 and a sealing element on the second connector half.

In step 6, the final position, shown in FIG. 12, the final interconnection of the connector halves 2, 3 and their components is provided by the locking sleeve 25 being moved onto the first connector half to a distinct end position. At the same time the protective films 13 covering the sealing means 11, 12 and the openings 8 of the connecting means 4, 5, are removed via drivers 26 by the locking sleeve 25 when this is moved and the sealing means and, thus, the openings 8 are pressed against each other, sealed against contamination.

A particularly preferred embodiment of the invention has been described and illustrated above, where the volume of the recesses 16, 17 is reduced when the sealing elements 11, 12 are moved into engagement and pressed against each other, sealed against contamination (steps 5, 6 above) so that the gas pressure in the recesses is increased and the gas, in the removal of the protective films 13, flows out in the environment to prevent contamination of the openings 8.

As an alternative to that embodiment, instead a volume increase of the recesses 16, 17 is provided, when the sealing elements are moved into engagement with each other, thus providing a decrease of the gas pressure therein. In this way, an underpressure is created relative to the pressure in the openings, so that gas is sucked out from the same; this too prevents contamination of the openings 8. The volume increase/pressure decrease can be achieved, for instance, by means such as elastic bellows, telescopic tubes etc, which are expanded in some other manner when the sealing elements 11, 12 are moved into engagement with each other.

It goes without saying that the invention should not be considered limited to the embodiment described above and illustrated in the drawings, with its described variants and alternatives, and can be modified in various ways within the scope of that stated in the appended claims.

The invention claimed is:

1. A method for contamination-free and/or sterile sealing between at least two interconnectable connecting means with opposing openings to allow, after interconnection, transfer of a fluid between the openings, sealing elements being arranged on the connecting means around the openings and provided with protective films covering the sealing elements and the openings, and adapted to be removed in the final interconnection, the method comprising:
    providing at least one sealing elements with at least one recess which extends wholly or partly around the associated opening, wherein said at least one recesses receives a gas;
    moving the sealing elements, which are interleaved with the protective films, into engagement with each other, when interconnecting the connecting means, to change a volume of the recess or recesses and, thus, change a pressure of the gas therein; and
    removing the protective films, whereby the gas creates by its pressure a flow which prevents penetration of contamination into the openings in the final interconnection of the connecting means,
    wherein the sealing elements are provided with at least two groups of recesses having different volumes, which cooperate in pairs and are positioned one outside the other, and in which the sealing elements, when moved against each other, reduce the different volumes of the recesses and, thus, increase the pressure of the gas therein differently, so that the gas, in the removal of the protective films, flows from the group of recesses with a highest pressure to the group/groups of recesses with a lower pressure.

2. The method as claimed in claim 1, in which the highest pressure is generated in an innermost group of recesses and a successively decreasing pressure is generated in an outer group/groups of recesses to force the gas in the direction of an environment.

3. The method as claimed in claim 1, in which the recesses in at least one group are divided into partial recesses to prevent all gas therein from flowing out before complete removal of the protective films.

4. The method as claimed in claim 1, in which there are arranged between the groups of recesses additional separate recesses with a limited extent to create, when starting to remove the protective films, an intensification of the gas flow in the direction of an environment.

5. The method as claimed in claim 1, in which at least one of the sealing elements is made elastically yieldable and is expanded and compressed, respectively, in the interconnection of the connecting means.

6. A device for contamination-free and/or sterile sealing between at least two interconnectable connecting means with opposing openings to allow, after interconnection, transfer of a fluid between the openings, the device having sealing elements which are arranged on the connecting means around the openings and are provided with protective films which cover the sealing elements and the openings, and are removable in the final interconnection, comprising:
    sealing elements wherein at least one of the sealing elements is provided with at least one recess, which extends wholly or partly around the associated opening, and receives a gas,
    wherein the sealing elements are interleaved with the protective films and are movable into engagement with each other, when interconnecting the connecting means, to change a volume of the recess or recesses and, thus, change a pressure of the gas therein, and, in the subsequent quick removal of the protective films, the gas creates by its pressure a flow which prevents penetration of contamination into the openings in the final interconnection of the connecting means,
    wherein the sealing elements are provided with at least two groups of recesses with different volumes, which cooperate in pairs and are positioned one outside the other, and wherein the sealing elements, when moved together, reduce the different volumes of the recesses and, thus, increase the pressure of the gas therein differently, and the gas, during removal of the protective films, flows from the group of recesses with the highest pressure to the group/groups of recesses with a lower pressure.

7. The device as claimed in claim 6, in which the highest pressure of the gas prevails in an innermost group of recesses and a successively decreasing pressure prevails in an outer group/groups of recesses to force the gas in the direction of an environment.

8. The device as claimed in claim 6, in which the recesses in at least one group are divided into partial recesses to prevent all gas therein from flowing out before complete removal of the protective films.

9. The device as claimed in claim 6, in which additional separate recesses with a limited extent are arranged between the groups of recesses to create, when starting to remove the protective films, an intensification of the gas flow in the direction of an environment.

10. The device as claimed in claim 6, in which at least one of the sealing elements is expandable and compressible, respectively, in the interconnection of the connecting means.

11. The device as claimed in claim 10, in which the at least one expandable and compressible sealing element has the form of an insert of an elastically yieldable material which is arranged in the associated connecting means.

12. The device as claimed in claim 6, in which there is arranged, outside each sealing element, a substantially circumferential seal of an elastically yieldable material on the associated connecting means, on which seals the protective films are sealingly arranged at their outer edge and which seals, interleaved with the protective films, are movable into engagement with each other in the interconnection of the connecting means.

13. A method for contamination-free and/or sterile sealing between at least two interconnectable connecting means with opposing openings to allow, after interconnection, transfer of a fluid between the openings, sealing elements being arranged on the connecting means around the openings and provided with protective films covering the sealing elements and the openings, and adapted to be removed in the final interconnection, the method comprising:

provingi at least one of the sealing elements with at least one recess which extends wholly or partly around the associated opening, wherein said at least one recess receives a gas;

moving the sealing elements, which are interleaved with the protective films, into engagement with each other, when interconnecting the connecting means, to change a volume of the recess or recesses and, thus, change a pressure of the gas therein; and removing the protective films, whereby the gas creates by its pressure a flow which prevents penetration of contamination into the openings in the final interconnection of the connecting means, wherein at least one of the connecting means is provided with an additional substantially circumferential seal arranged outside said sealing element.

14. The method as claimed in claim 13, wherein at least one of the sealing elements has a plurality of groups of recesses, and wherein a highest pressure is generated in an innermost group of recesses and a successively decreasing pressure is generated in an outer group/groups of recesses to force the gas in the direction of an environment.

15. The method as claimed in claim 13,
wherein at least one of the sealing elements has a plurality of groups of recesses, and
wherein the recesses in at least one group of recesses are divided into partial recesses to prevent all gas therein from flowing out before complete removal of the protective films.

16. The method as claimed in claim 13, wherein at least one of the sealing elements has a plurality of groups of recesses, and wherein there arranged between the groups of recesses additional separate recesses with a limited extent to create, when starting to remove the protective films, an intensification of the gas flow in the direction of an environment.

17. The method as claimed in claim 13, in which at least one of the sealing elements is made elastically yieldable and is expanded and compressed, respectively, in the interconnection of the connecting means.

18. A method as claimed in claim 13, in which the sealing elements are moved into engagement with each other to reduce the volume of the recess or recesses of the sealing elements and, thus increase the pressure of the gas therein, and in which, in the subsequent quick removal of the protective films, the gas flows out of the recesses to prevent penetration of contamination into the openings in the final interconnection of the connecting means.

19. A method as claimed in claim 13, in which the sealing elements are moved into engagement with each other to increase the volume of the recess or recesses of the sealing elements and, thus reduce the pressure of the gas therein, and in which, in the subsequent quick removal of the protective films, the gas sucks in additional gas to create a flow which prevents penetration of contamination into the openings in the final interconnection of the connecting means.

20. A device for contamination-free and/or sterile sealing between at least two interconnectable connecting means with opposing openings to allow, after interconnection, transfer of a fluid between the openings, the device having sealing elements which are arranged on the connecting means around the openings and are provided with protective films which cover the sealing elements and the openings, and are removable in the final interconnection, comprising:

sealing elements wherein at least one of the sealing elements is provided with at least one recess, which extends wholly or partly around the associated opening, and receives a gas; and an additional substantially circumferential seal arranged outside at least one of the sealing elements, wherein the sealing elements are interleaved with the protective films and are movable into engagement with each other, when interconnecting the connecting means, to change a volume of the recess or recesses and, thus, change a pressure of the gas therein, and, in the subsequent quick removal of the protective films, the gas creates by its pressure a flow which prevents penetration of contamination into the openings in the final interconnection of the connecting means.

21. The device as claimed in claim 20, wherein at least one of the sealing elements has a plurality of groups of recesses, and wherein a highest pressure of the gas prevails in an innermost group of recesses and a successively decreasing pressure prevails in an outer group/groups of recesses to force the gas in the direction of an environment.

22. The device as claimed in claim 20, wherein at least one of the sealing elements has a plurality of groups of recesses, and wherein the recesses in at least on group of recesses are divided into partial recesses to prevent all gas therein from flowing out before complete removal of the protective films.

23. The device as claimed in claim 20, wherein at least one of the sealing elements has a plurality of groups of recesses, and wherein additional separate recesses with a limited extent are arranged between the groups of recesses to create, when starting to remove the protective films, an intensification of the gas flow in the direction of an environment.

24. The device as claimed in claim 20, in which at least one of the sealing elements is expandable and compressible, respectively, in the interconnection of the connecting means.

25. The device as claimed in claim 24, in which the at least one expandable and compressible sealing element has the form of an insert of an elastically yieldable material which is arranged in the associated connecting means.

26. A device as claimed in claim 20, in which the sealing elements are movable into engagement with each other to reduce the volume of the recess or recesses of the sealing elements and, thus, increase the pressure of the gas therein, and in which, in the subsequent quick removal of the protective films, the gas is caused to flow out of the recess or recesses and, thus, prevent penetration of contamination into the openings in the final interconnection of the connecting means.

27. A device as claimed in claim 20, in which the sealing elements are movable into engagement with each other to increase the volume of the recess or recesses of the sealing elements and, thus, decrease the pressure of the gas therein, and in which, in the subsequent quick removal of the protective films, the gas is caused to suck in additional gas and, thus, prevent penetration of contamination into the openings in the final interconnection of the connecting means.

* * * * *